United States Patent
Munayyer et al.

(10) Patent No.: US 6,514,520 B2
(45) Date of Patent: *Feb. 4, 2003

(54) STABILIZED ANTIHISTAMINE SYRUP

(75) Inventors: Farah J. Munayyer, West Caldwell, NJ (US); Frank Guazzo, Bridgewater, NJ (US); Elliot I. Stupak, West Caldwell, NJ (US); Imtiaz A. Chaudry, North Caldwell, NJ (US); Joel A. Sequeira, Edison, NJ (US)

(73) Assignee: Schering Corporation, Kenilworth, NJ (US)

( * ) Notice: Subject to any disclaimer, the term of this patent is extended or adjusted under 35 U.S.C. 154(b) by 0 days.

This patent is subject to a terminal disclaimer.

(21) Appl. No.: 09/899,764

(22) Filed: Jul. 5, 2001

(65) Prior Publication Data

US 2002/0132805 A1 Sep. 19, 2002

Related U.S. Application Data

(63) Continuation of application No. 09/708,188, filed on Nov. 8, 2000, now abandoned, which is a continuation of application No. 09/616,866, filed on Jul. 14, 2000, now abandoned, which is a continuation of application No. 09/088,128, filed on Jun. 1, 1998, now Pat. No. 6,132,758.

(51) Int. Cl.$^7$ .......................... A61K 9/00; A61K 31/435
(52) U.S. Cl. ................ 424/439; 424/400; 514/290; 546/93
(58) Field of Search .................... 514/290; 546/93; 424/400, 439

(56) References Cited

U.S. PATENT DOCUMENTS

| | | | |
|---|---|---|---|
| 4,659,716 A | 4/1987 | Villani et al. | 514/290 |
| 4,783,465 A | 11/1988 | Sunshine et al. | 514/255 |
| 4,975,426 A | 12/1990 | Sunshine et al. | 514/159 |
| 5,759,579 A | 6/1998 | Singh et al. | 424/485 |
| 5,912,007 A | 6/1999 | Pan et al. | 424/440 |
| 5,939,426 A | 8/1999 | McCullough | 514/290 |
| 6,132,758 A | * 10/2000 | Munayyer et al. | 424/439 |

FOREIGN PATENT DOCUMENTS

| | | |
|---|---|---|
| EP | 0 620 001 A1 | 10/1994 |
| WO | WO 98/18470 | 5/1998 |
| WO | WO 98/24414 | 6/1998 |

OTHER PUBLICATIONS

*Drug Facts and Comparisons*, 1998 Ed., Facts and Comparisons, St. Louis, Missouri, p. 2832.
*The United States Pharmacopeia, The United States Formulary*, United States Pharmacopeial Convention, Inc., Rockville, Maryland, 1989, p. 1990.
*Remington's Pharmaceutical Sciences*, 18$^{th}$ Ed., Mack Publishing Company, Easton, Pennsylvania, 1990, pp. 1519–1520 and 1527–1529.

* cited by examiner

*Primary Examiner*—Richard L. Raymond
(74) *Attorney, Agent, or Firm*—Robert A. Franks

(57) ABSTRACT

An antihistaminic syrup is stabilized against degradation of the active ingredient, by the addition of and about 0.05 to about 5 mg/mL of an aminopolycarboxylic acid such as a salt of ethylenediaminetetraacetic acid.

20 Claims, No Drawings

STABILIZED ANTIHISTAMINE SYRUP

CROSS-REFERENCE TO RELATED APPLICATIONS

This application is a continuation of Ser. No. 09/708,188 filed Nov. 8, 2000 and now abandoned, which is a continuation of Ser. No. 09/616,866 filed Jul. 14, 2000 and now abandoned, which itself is a continuation of Ser. No. 09/088,128 filed Jun. 1, 1998 and now U.S. Pat. No. 6,132,758 granted Oct. 17, 2000.

INTRODUCTION TO THE INVENTION

The present invention pertains to the field of liquid pharmaceutical formulations, and more particularly to syrup formulations containing antihistamines.

Syrup formulations are commonly used for delivery of pharmacological agents, particularly where the agents are to be delivered to pediatric patients. Traditional syrups are concentrated solutions of sugar (generally sucrose) in purified water, such as Syrup, NF prepared with 850 grams sucrose and sufficient water to make 1000 mL according to the procedure given in the official monograph at page 1990 of *NF XVII The National Formulary*, United States Pharmacopeial Convention, Inc., Rockville, Md. U.S.A., 1990. However, for purposes of the present invention, the term "syrup" will also encompass those liquid formulations having a sweet taste provided wholly or partly by artificial sweeteners, such as saccharin, sorbitol, aspartame, sodium cyclamate and the like, for avoidance of dental and medical problems which may be aggravated by higher caloric sweeteners. As is well appreciated in the art, syrups frequently are flavored, such as with fruit or mint flavors, usually for purposes of masking an unpleasant taste caused by the presence of a dissolved or suspended pharmacologically active substance. A pleasant taste is particularly important when the formulation is intended for ingestion by children. Typical flavoring agents which are commonly used in sweetened pharmaceuticals, foods, candies, beverages and the like are also useful in the present invention; these materials impart flavors such as grape, cherry, citrus, peach, strawberry, bubble gum, peppermint and many others.

Syrups frequently must contain antimicrobial components to ensure safe storage without the proliferation of pathogenic molds, yeasts, bacteria and the like; a typical antimicrobial deemed suitable for use in foods and other ingestable substances is sodium benzoate. In addition, those syrups which do not contain sugar, or which contain a mixture of sugar and another sweetener, may contain thickening agents (such as a hydroxypropyl methylcellulose, some forms of which are available from Dow Chemical, Midland, Mich. USA under the METHOCEL trademark) to provide a viscous mouth-feel similar to that of a traditional syrup.

An example of a currently marketed syrup contains 1 mg/mL of the antihistaminic drug loratadine, together with citric acid, artificial flavor, glycerin, propylene glycol, sodium benzoate, sucrose and water; this formulation typically has a pH value between about 2 and 4. However, under certain storage conditions involving contact with the air, losses of loratadine content, and a concomitant generation of impurities, have occurred. Similar problems can occur with formulations containing other, chemically related, drugs, such as descarboethoxyloratadine and azatadine.

J. S. Nairn, "Solutions, Emulsions, Suspensions and Extracts," Chapter 83 in A. R. Gennaro, Ed., *Remington's Pharmaceutical Sciences*, 18th Ed., Mack Publishing Co., Easton Penn. U.S.A., 1990 at pages 1519–1520 discusses the problem of active agent stability in aqueous media. It is stated that trace metal-initiated oxidation reactions can be minimized through the use of citric acid or EDTA sequestering agents.

It is desired to provide a storage-stable syrup formulation of loratadine or related antihistaminic components, which contains only components recognized as being safe for human ingestion.

SUMMARY OF THE INVENTION

In accordance with the invention, there is provided a syrup formulation containing loratadine or a chemically related antihistamine, including any pharmaceutically acceptable salt thereof, together with a stabilizing amount of an aminopolycarboxylic acid. Suitable aminopolycarboxylic acids include ethylenediaminetetraacetic acid ("EDTA") and salts thereof, such as the disodium salt. The acid or salt is usually present in the formulation in concentrations about 0.05 mg/mL to about 5 mg/mL.

DETAILED DESCRIPTION OF THE INVENTION

Loratadine is the drug name given to the compound known as ethyl 4-(8-chloro-5,6-dihydro-11H-benzo[5,6]cyclohepta[1,2-b]pyridin-11-ylidene)-1-piperidinecarboxylate and having the empirical formula $C_{22}H_{23}ClN_2O_2$. A structure for this compound is:

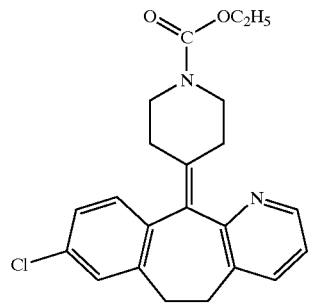

The compound descarboethoxyloratadine is an antihistaminic active metabolite of loratadine, having the following structure:

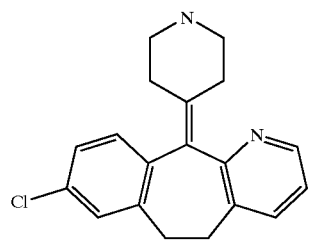

A closely related antihistamine is azatadine, having the following structural formula:

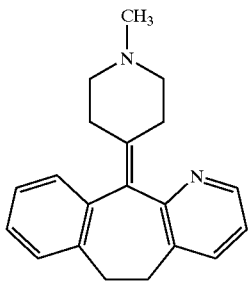

Degradation of syrup formulations containing loratadine or related antihistamines is observed during storage stability testing, as evidenced by declining concentrations of the active ingredient and a concomitant formation of impurities. Two of the impurities which form in loratadine syrups have been identified as 2-Hydroxymethyl loratadine ("2-HML") and 4-Hydroxymethyl loratadine ("4-HML"), while other unidentified impurities occur regularly and have been collectively denoted as "Group A"; these materials number about 5 to 7 and elute together in an HPLC analysis, at retention times which indicate a higher polarity than that of loratadine. The severity of the degradation may be at least approximately related to the volume in a product bottle which is not filled with syrup, i.e., the "headspace." As it is not practical to fill each bottle completely to the top, a test has been conducted where the headspace was filled with nitrogen gas; results were inconclusive, possibly due to the unavoidable oxygen permeability of the polymeric bottle closure.

Another test was conducted, wherein common antioxidant additives were incorporated into the syrup. Ideally, the antioxidant will be soluble in the syrup and is safe for use in foods and pharmaceutical preparations. Among the water-soluble materials, ascorbic acid at 0.1 and 1 mg/mL was found to somewhat reduce degradation, but also caused an unacceptable strong color change in the product, while sodium bisulfite imparted a pungent, disagreeable odor to the syrup. The oil-soluble antioxidants butylated hydroxytoluene and tocopherol were not soluble in the syrup, so also were not found acceptable.

It has been found that the addition of small amounts of an aminopolycarboxylic acid, the term specifically including salts of the acids, can stabilize the syrups against degradation. Useful aminopolycarboxylic acids and salts thereof are those which are safe for ingestion and have sufficient solubility in the syrup formulations to make a stable single phase composition. Commercially available compounds which could be used include iminodiacetic acid, methyliminodiacetic acid, nitrilotriacetic acid, ethylenediaminetetraacetic acid ("EDTA"), diethylenetriaminepentaacetic acid, 1,2-diaminocyclohexane-tetraacetic acid, N-hydroxyethylenediaminetriacetic acid and related compounds. Mixtures of two or more of the foregoing are suitable for use. From the aspects of ready availability, safety, efficacy and cost, the alkali metal salts of EDTA are presently preferred, and the remainder of this description will focus on those materials.

An aminopolycarboxylic acid or salt will typically be present in a syrup at about 0.05 mg/mL to about 5 mg/mL. More preferably, the level of aminopolycarboxylic acid will be about 0.1 mg/mL to about 1 mg/mL. As with any additive component in a formulation intended for ingestion, it is desirable to incorporate the minimum level which will yield the desired result. This level can be readily determined by means of an accelerated storage stability test, in which packages of the final product are stored at elevated temperatures above the usual storage temperatures to which the product is expected to be exposed; the present inventors have used temperatures up to 55° C. for this purpose, although such temperatures tend to cause a minor discoloration (darkening) of the syrups, probably due to some carmelization of the contained sucrose. It is expected that most drug degradation reactions will be accelerated by the elevated temperature. At predetermined intervals, some of the packages are opened and analyzed to determine the amount of active ingredients and impurities present in the formulation.

Antihistaminic syrup formulations frequently also contain other drugs, for obtaining more than one therapeutic result from a single dose. Typical drug substances included with the antihistamine are sympathomimetic amine decongestants, such as pseudoephedrine or phenylpropanolamine (for relief of the upper airway congestion often accompanying disorders such as rhinitis and upper respiratory infections), and analgesics, such as aspirin, acetaminophen, ibuprofen, naproxen or ketoprofen (for relief of pain and, except in the case of acetaminophen, for reducing inflammation). Antitussives, such as codeine, hydrocodone or dextromethorphan, for relief from coughing, and expectorants such as guaifenesin, for increasing cough productivity, also are included in combination products. Any of these additional ingredients, including salts thereof and other drugs from the same therapeutic classes, are suitable for inclusion in the syrups of the present invention.

The invention will be further described by means of the following examples, which are not intended to limit the scope of the invention as defined by the appended claims. Where the term "percent" is used herein, it is intended to represent percent by weight, unless the context clearly evidences otherwise.

EXAMPLE 1

A syrup was formulated to contain the following ingredients, wherein amounts of all except water are expressed in milligrams.

| Ingredient | Amount |
| --- | --- |
| Loratadine, micronized | 1 |
| Citric acid | 8.78 |
| Flavoring agent | 2.5 |
| Glycerin | 100 |
| Propylene glycol | 100 |
| Sodium benzoate | 1 |
| Disodium EDTA | 0.25 |
| Sucrose | 600 |
| Water | to make 1.0 mL |

This syrup is prepared using the following procedure: (a) about 80 percent of the water is placed in a vessel, heated to 75–85° C., charged with the sugar and stirred to form a solution; (b) the citric acid is charged to the solution and stirring is continued to form a solution, then the sodium benzoate is added and dissolved; (c) the solution is cooled to 30–35° C., with continued stirring, and the disodium EDTA is added and dissolved; (d) the glycerin is added and stirring continued while the solution cools to 25–30° C.; (e) in a separate vessel, the propylene glycol and loratadine are combined and stirred to form a solution (note that the use of micronized loratadine particles decreases the time required to accomplish dissolution), then the flavoring agent is added and stirred to achieve homogeneity; (f) the product of step e is combined with the product of step d, with stirring to ensure homogeneity, and sufficient water is added to provide the proper formulation weight; and (g) the resulting syrup is passed through clarifying filters. The syrup is a clear, colorless liquid (which could readily be colored as desired, such as by adding a suitable pharmaceutically acceptable water-soluble dye to the sugar solution of step a) and is denoted Sample A.

Another syrup is similarly formulated, except that it further contains 1 mg/mL of the disodium salt of EDTA. This is denoted Sample B.

Twenty five mL portions of the two syrups are placed into 50 mL flint glass vials, then sealed with rubber stoppers and aluminum caps. The sealed vials are stored at 55° C. until their removal and analysis by high performance liquid chromatography. Results of the analyses are as follows, where "NQ" indicates a result below the limit of quantification (0.1%) but above the limit of detection (0.02%):

| Sample | Storage (weeks) | Percent Degradation Products | | |
|---|---|---|---|---|
| | | 2-HML | 4-HML | Total |
| A | 3 | 0.23 | 0.19 | 0.42 |
| | 6 | 0.33 | 0.32 | 0.81[a] |
| B | 3 | 0.11 | NQ | 0.11 |
| | 6 | 0.10 | NQ | 0.10 |
| | 12 | 0.15 | 0.14 | 0.62[b] |

[a]Sample contained 0.16% of an unidentified degradation product
[b]Sample contained two unidentified degradation products at levels of 0.21% and 0.12%

These results indicate a significant inhibition by EDTA of the degradation of loratadine during the severe storage conditions of the test.

EXAMPLE 2

Sample A from the preceding example and similarly prepared syrups which also contain 0.1, 0.25, 0.5 or 0.75 mg/mL of disodium EDTA are packaged as in the prior example, and stored and tested similarly. The following results are obtained, where "ND" indicates a concentration below the limit of detection previously stated.

| EDTA (mg/mL) | Storage (weeks) | Percent Degradation Products | | |
|---|---|---|---|---|
| | | 2-HML | 4-HML | Total |
| 0 | 3 | 0.25 | 0.21 | 0.69[a] |
| | 6 | 0.29 | 0.24 | 0.67[b] |
| | 9 | 0.49 | 0.53 | 1.54[c] |
| 0.1 | 3 | NQ | NQ | NQ |
| | 6 | 0.10 | NQ | 0.10 |
| | 9 | 0.12 | 0.11 | 0.33[d] |
| 0.25 | 3 | NQ | NQ | NQ |
| | 6 | NQ | NQ | NQ |
| | 9 | 0.10 | NQ | 0.10 |
| 0.5 | 3 | NQ | ND | NQ |
| | 6 | 0.10 | ND | 0.10 |
| | 9 | 0.11 | 0.10 | 0.21 |
| 0.75 | 3 | NQ | NQ | NQ |
| | 6 | 0.10 | ND | 0.10 |
| | 9 | 0.10 | 0.10 | 0.20 |

[a]Sample contained 0.11% of Group A degradation products and 0.12% of an unidentified degradation product
[b]Sample contained 0.14% of an unidentified degradation product
[c]Sample contained three unidentified degradation products at levels of 0.17%, 0.13% and 0.22%
[d]Sample contained 0.10% of an unidentified degradation product These results suggest that 0.25 percent disodium EDTA would be a reasonable level for storage protection of the tested syrup.

EXAMPLE 3

A stabilized syrup is formulated according to the previously described general procedure to contain the following ingredients, wherein amounts of all except water are expressed in milligrams.

| Ingredient | Amount |
|---|---|
| Loratadine, Micronized | 1 |
| Citric acid | 8.78 |
| Flavoring agent | 1.5 |
| Glycerin | 100 |
| Propylene glycol | 100 |
| Sodium benzoate | 1 |
| Disodium EDTA | 0.25 |
| Coloring agent | 1 |
| Sucrose | 400 |
| Water | to make 1.0 mL |

This syrup is found to exhibit acceptable storage stability.

EXAMPLE 4

A stabilized syrup is formulated according to the previously described general procedure to contain the following ingredients, wherein amounts of all except water are expressed in milligrams.

| Ingredient | Amount |
|---|---|
| Loratadine, micronized | 1 |
| Citric acid | 0.48 |
| Sodium citrate | 0.6 |
| Flavoring agent | 1.5 |
| Glycerin | 350 |
| Propylene glycol | 100 |
| Sorbitol | 150 |
| Sodium benzoate | 1 |
| Disodium EDTA | 0.25 |
| Sodium cyclamate | 0.75 |
| Hydroxypropyl methylcellulose | 0.5 |
| Coloring agent | 1 |
| Water | to make 1.0 mL |

This syrup is found to exhibit acceptable storage stability. METHOCEL™ K100M, K4M and A4M from Dow Chemical are among the hydroxypropyl methylcellulose products which are suitable for use in the invention; substituting the various available products can cause syrup viscosity changes, so experiments should be conducted to determine the appropriate grade and amount needed to prepare a given syrup with desired properties.

EXAMPLE 5

A stabilized syrup is formulated according to the previously described general procedure to contain the following ingredients, wherein amounts of all except water are expressed in milligrams.

| Ingredient | Amount |
| --- | --- |
| Loratadine, micronized | 1 |
| Citric acid | 0.48 |
| Sodium citrate | 0.6 |
| Flavoring agent | 1 |
| Glycerin | 350 |
| Propylene glycol | 100 |
| Sorbitol | 150 |
| Sodium benzoate | 1 |
| Disodium EDTA | 0.25 |
| Saccharin | 0.75 |
| Hydroxypropyl methylcellulose | 0.5 |
| Water | to make 1.0 mL |

This syrup is found to exhibit acceptable storage stability.

EXAMPLE 6

A stabilized syrup is formulated according to the previously described general procedure to contain the following ingredients, wherein amounts of all except water are expressed in milligrams.

| Ingredient | Amount |
| --- | --- |
| Loratadine | 1 |
| Citric acid | 0.48 |
| Sodium citrate | 0.6 |
| Flavoring agent | 2.5 |
| Glycerin | 450 |
| Sorbitol | 250 |
| Propylene glycol | 100 |
| Sodium benzoate | 1 |
| Disodium EDTA | 0.25 |
| Water | to make 1.0 mL |

This syrup is found to exhibit acceptable storage stability.

EXAMPLE 7

A stabilized syrup is formulated according to the previously described general procedure, but substituting descarboethoxyloratadine for loratadine, to contain the following ingredients, wherein amounts of all except water are expressed in milligrams.

| Ingredient | Amount |
| --- | --- |
| Descarboethoxyloratadine | 1 |
| Citric acid | 8.78 |
| Flavoring agent | 2.5 |
| Glycerin | 100 |
| Propylene glycol | 100 |
| Sodium benzoate | 1 |
| Disodium EDTA | 0.25 |
| Sucrose | 400 |
| Water | to make 1.0 mL |

This syrup is found to exhibit acceptable storage stability.

EXAMPLE 8

A stabilized syrup is formulated according to the previously described general procedure, but substituting azatadine for loratadine, to contain the following ingredients, wherein amounts of all except water are expressed in milligrams.

| Ingredient | Amount |
| --- | --- |
| Azatadine | 1 |
| Citric acid | 8.78 |
| Flavoring agent | 2.5 |
| Glycerin | 100 |
| Propylene glycol | 100 |
| Sodium benzoate | 1 |
| Sucrose | 600 |
| Water | to make 1.0 mL |

This syrup is found to exhibit acceptable storage stability.

EXAMPLE 9

A stabilized syrup for pedriatric use is formulated according to the previously described general procedure to contain the following ingredients, wherein amounts of all except water are expressed in milligrams.

| Ingredient | Amount |
| --- | --- |
| Loratadine | 0.5 |
| Pseudoephedrine sulfate | 3 |
| Acetaminophen | 32 |
| Dextromethorphan hydrobromide | 1.5 |
| Citric acid | 8.78 |
| Flavoring agent | 1.5 |
| Glycerin | 100 |
| Propylene glycol | 100 |
| Sodium benzoate | 1 |
| Disodium EDTA | 0.25 |
| Coloring agent | 1 |
| Sucrose | 400 |
| Water | to make 1.0 mL |

This syrup is found to exhibit acceptable storage stability.

What is claimed is:

1. An antihistaminic syrup formulation comprising descarboethoxyloratadine and about 0.05 to about 5 mg/mL of an aminopolycarboxylic acid or a salt thereof.

2. The syrup of claim 1, wherein the aminopolycarboxylic acid is selected from the group consisting of: iminodiacetic acid; methyliminodiacetic acid; nitrilotriacetic acid; ethylenediaminetetraacetic acid; diethylenetriaminepentaacetic acid; 1,2-diaminocyclohexane-tetraacetic acid; N-hydroxyethylenediaminetriacetic acid; and any combination of two or more thereof.

3. The syrup of claim 1, wherein the aminopolycarboxylic acid comprises ethylenediaminetetraacetic acid.

4. The syrup of claim 1, in which the aminopolycarboxylic acid comprises about 0.1 to 1 mg/mL.

5. The syrup of claim 3, in which the aminopolycarboxylic acid comprises about 0.25 to about 0.5 mg/mL.

6. The syrup of claim 1, further containing a therapeutically effective amount of a decongestant, an analgesic, an antitussive, an expectorant, or any combination of two or more thereof.

7. The syrup of claim 1, further containing a decongestant selected from the group consisting of pseudoephedrine and phenylpropanolamine.

8. The syrup of claim 1, further containing the decongestant pseudoephedrine.

9. An antihistaminic syrup comprising descarboethoxyloratadine and an aminopolycarboxylic acid or a salt thereof.

10. The antihistaminic syrup of claim 9, wherein the aminopolycarboxylic acid or salt is present in an amount sufficient to inhibit degradation of said descarboethoxyloratadine.

11. The antihistaminic syrup of claim 9, wherein the aminopolycarboxylic acid is selected from the group consisting of: iminodiacetic acid; methyliminodiacetic acid; nitrilotriacetic acid; ethylenediaminetetraacetic acid; diethylenetriaminepentaacetic acid; 1,2-diaminocyclohexane-tetraacetic acid; N-hydroxyethylenediaminetriacetic acid; and a combination of two or more thereof.

12. The antihistaminic syrup of claim 9, wherein the aminopolycarboxylic acid comprises ethylenediaminetetraacetic acid.

13. The antihistaminic syrup of claim 12, wherein the ethylenediaminetetraacetic acid or salt is present in an amount sufficient to inhibit degradation of said descarboethoxyloratadine.

14. A syrup formulation comprising descarboethoxyloratadine and about 0.05 to about 5 mg/mL of an aminopolycarboxylic acid or a salt thereof, sufficient to inhibit degradation of said descarboethoxyloratadine.

15. The syrup of claim 14, wherein the aminopolycarboxylic acid comprises ethylenediaminetetraacetic acid.

16. The syrup of claim 15, wherein the ethylenediamine tetraacetic acid is present in an amount of about 0.25 to about 0.5 mg/mL.

17. The syrup of claim 14, further comprising a therapeutically effective amount of a decongestant, analgesic, antitussive, expectorant or a combination of two or more thereof.

18. The syrup of claim 14, further comprising pseudoephedrine or a salt thereof.

19. The syrup of claim 18, further comprising an analgesic.

20. The syrup of claim 14, further comprising a decongestant and an analgesic.

* * * * *

(12) EX PARTE REEXAMINATION CERTIFICATE (5544th)

United States Patent
Munayyer et al.

(10) Number: US 6,514,520 C1
(45) Certificate Issued: *Oct. 3, 2006

(54) STABILIZED ANTIHISTAMINE SYRUP

(75) Inventors: Farah J. Munayyer, West Caldwell, NJ (US); Frank Guazzo, Bridgewater, NJ (US); Elliot I. Stupak, West Caldwell, NJ (US); Imtiaz A. Chaudry, North Caldwell, NJ (US); Joel A. Sequeira, Edison, NJ (US)

(73) Assignee: Schering Corporation, Kenilworth, NJ (US)

Reexamination Request:
No. 90/006,820, Oct. 22, 2003

Reexamination Certificate for:
Patent No.: 6,514,520
Issued: Feb. 4, 2003
Appl. No.: 09/899,764
Filed: Jul. 5, 2001

( * ) Notice: This patent is subject to a terminal disclaimer.

Related U.S. Application Data

(63) Continuation of application No. 09/708,188, filed on Nov. 8, 2000, now abandoned, which is a continuation of application No. 09/616,866, filed on Jul. 14, 2000, now abandoned, which is a continuation of application No. 09/088,128, filed on Jun. 1, 1998, now Pat. No. 6,132,758.

(51) Int. Cl.
*A61K 9/00* (2006.01)
*A61K 31/435* (2006.01)
*A61K 47/00* (2006.01)
*A61K 31/44* (2006.01)

(52) U.S. Cl. ................ 424/439; 424/400; 514/290; 546/93

(58) Field of Classification Search ........... 424/400, 424/439; 514/290; 546/93
See application file for complete search history.

(56) References Cited

U.S. PATENT DOCUMENTS 6,383,471 B1 * 5/2002 Chen et al. .............. 424/45
6,790,847 B1 * 9/2004 Walch .................. 424/78.05

FOREIGN PATENT DOCUMENTS

EP     0 872 236 A1   10/1998
WO    WO 97/15307    * 5/1997

* cited by examiner

*Primary Examiner*—Brenda Coleman

(57) ABSTRACT

An antihistaminic syrup is stabilized against degradation of the active ingredient, by the addition of and about 0.05 to about 5 mg/mL of an aminopolycarboxylic acid such as a salt of ethylenediaminetetraacetic acid.

EX PARTE REEXAMINATION CERTIFICATE ISSUED UNDER 35 U.S.C. 307

NO AMENDMENTS HAVE BEEN MADE TO THE PATENT

AS A RESULT OF REEXAMINATION, IT HAS BEEN DETERMINED THAT:

The patentability of claims 1–20 is confirmed.

* * * * *